United States Patent  (10) Patent No.: US 9,179,997 B2
Cho et al.  (45) Date of Patent: Nov. 10, 2015

(54) THERMOCHROMIC POLYVINYL ALCOHOL BASED HYDROGEL ARTERY

(71) Applicant: St. Jude Medical, Cardiology Division, Inc., St. Paul, MN (US)

(72) Inventors: Eunhee Cho, Maplewood, MN (US); Valentine Kozov, Plymouth, MN (US); Sukanya Varadharajan, Maplewood, MN (US); Steven N. Willard, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 23 days.

(21) Appl. No.: 13/786,727

(22) Filed: Mar. 6, 2013

(65) Prior Publication Data

US 2014/0257275 A1 Sep. 11, 2014

(51) Int. Cl.
*A61F 2/06* (2013.01)
*A61B 18/00* (2006.01)
*A61B 5/01* (2006.01)
*A61L 27/16* (2006.01)
*A61L 27/50* (2006.01)
*A61B 10/00* (2006.01)
*A61B 17/00* (2006.01)

(52) U.S. Cl.
CPC . *A61F 2/06* (2013.01); *A61B 5/015* (2013.01); *A61B 18/00* (2013.01); *A61L 27/16* (2013.01); *A61L 27/507* (2013.01); *A61B 2010/0006* (2013.01); *A61B 2017/00084* (2013.01)

(58) Field of Classification Search
USPC ................... 264/28, 40.1, 233, 234; 607/102; 424/10.3
See application file for complete search history.

(56) References Cited

U.S. PATENT DOCUMENTS

| 3,650,277 | A | | 3/1972 | Sjostrand et al. |
| 4,658,819 | A | | 4/1987 | Harris et al. |
| 4,663,358 | A | * | 5/1987 | Hyon et al. ...................... 521/64 |
| 5,035,694 | A | | 7/1991 | Kasprzyk et al. |
| 5,255,679 | A | | 10/1993 | Imran |

(Continued)

FOREIGN PATENT DOCUMENTS

| EP | 0107055 | 5/1984 |
| KR | 20130020087 | 2/2013 |

(Continued)

OTHER PUBLICATIONS

Dibona, Gerald F., Neural Control of the Kidney: Past, Present, and Future, Hypertension Journal of the American Heart Association, vol. 41, Mar. 2003, Part II, 621-624.

(Continued)

*Primary Examiner* — Atul P. Khare
(74) *Attorney, Agent, or Firm* — Armstrong Teasdale LLP (57) ABSTRACT

A method of creating a thermochromic artificial blood vessel includes physically cross-linking a polyvinyl alcohol solution in a mold shaped to mimic a blood vessel to create an artificial blood vessel. The artificial tissue is then chemically cross-linked with a solution including a chemical cross-linking reagent. A coagulation solution is then applied to the artificial blood vessel to both inhibit the chemical cross-linking and promote physical cross-linking of the artificial blood vessel. The artificial blood vessel can be used to test an ablation catheter. The vessel, when heated by the ablation catheter, changes color and/or transparency at locations where the temperature of artificial blood vessel increases.

16 Claims, 4 Drawing Sheets

(56) References Cited

U.S. PATENT DOCUMENTS

| | | | |
|---|---|---|---|
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 5,972,375 A | 10/1999 | Truter et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,231,605 B1 * | 5/2001 | Ku ................ 623/11.11 |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,294,143 B2 * | 11/2007 | Francischelli ................ 607/105 |
| 7,297,143 B2 * | 11/2007 | Woloszko et al. ............. 606/41 |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 8,663,211 B2 * | 3/2014 | Fourkas et al. ................ 606/21 |
| 2002/0068885 A1 | 6/2002 | Harhen et al. |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0255478 A1 | 10/2008 | Burdette |
| 2008/0274054 A1 * | 11/2008 | Chiou et al. ................... 424/9.1 |
| 2008/0312644 A1 * | 12/2008 | Fourkas et al. ................ 606/22 |
| 2009/0076409 A1 | 3/2009 | Wu et al. |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0039813 A1 * | 2/2012 | Tansil et al. ................... 424/9.6 |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0323233 A1 | 12/2012 | Maguire et al. |
| 2013/0116771 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 97/45157 | 12/1997 |
| WO | 00/66020 | 11/2000 |
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Dibona, Gerald F., Renal Innervation and Denervation: Lessons from Renal Transplantation Reconsidered, Artificial Organs, vol. 11, No. 6, 1987, 457-462.

Dibona, Gerald F., Role of the Renal Nerves in Renal Sodium Retention and Edema Formation, Trans Am Clin Climatol Assoc. 1990; 101: 38-45.

Dibona, Gerald F., Sympathetic Nervous System and Hypertension, Hypertension Journal of the American Heart Association, 2013; 61: 556-560.

Dibona, Gerald F., Sympathetic Nervous System and the Kidney in Hypertension, Curr Opin Nephrol Hypertens. Mar. 2002;11(2):197-200.

Dibona, Gerald F., The Sympathetic Nervous System and Hypertension, Hypertension Journal of the American Heart Association, Vo. 43, Feb. 2004, 147-150.

Doumas, Michael et al, Interventional Management of Resistant Hypertension, The Lancet, vol. 373, Apr. 11, 2009, pp. 1228-1230.

Dubuc, Marc et al, Feasibility of Cardiac Cryoablation Using a Transvenous Steerable Electrode Catheter, Journal of Interventional Cardiac Electrophysiology, 1998, 2: 285-292.

Elmula, Fadl et al, Renal Sympathetic Denervation in Patients With Treatment-Resistant Hypertension After Witnessed Intake of Medi- (56) References Cited

OTHER PUBLICATIONS cation Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:I-13 (1982).
Grassi, Guido et al, Baroreflex Control of Sympathetic Nerve Activity in Essential and Secondary Hypertension, Hypertension Journal of the American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.

Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May. 1994;266(5 Pt 2):F738-F745.
Hoobler, S.W. et al, The Effects of Splanchnicectomy on the Blood Pressure in Hypertension, Circulation Journal of the American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.
Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, (2013) 0: 1-8.
Huang, Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of the American Heart Association, 1998;32:249-254.
Humpreys, Michael H., Renal Nerves and CKD: Is Renal Denervation the Answer?, Journal of the American Socity of Nephrology, 2012, 23: 1-3.
International Search Report and Written Opinion for Application No. PCT/US2010/054637.
International Search Report and Written Opinion for Application No. PCT/US2010/054684.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.

(56) References Cited

OTHER PUBLICATIONS

Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the SYMPLICITY HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After SYMPLICITY HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of the American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal but Not Cardiac Sympathetic Activity in Humans; Hypertension Journal of the American Heart Association, 1991;18:575-582.

(56) References Cited

OTHER PUBLICATIONS

Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of the American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14 (4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of the American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of the American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of the American Heart Association, 1998;31:823-829.

(56) References Cited

OTHER PUBLICATIONS

Poutasse, Eugene F., Surgical Treatment of Renal Hypertension, American Journal of Surgery, vol. 107, Jan. 1964, 97-103.

Pugsley, M.K. et al, The Vascular System an Overview of Structure and Function, Journal of Pharmacological and Toxicological Methods 44 (2000) 333-340.

Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.

Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.

Rippy, Marian K. et al, Catheter-Based Renal Sympathetic Denervation: Chronic Preclinical Evidence for Renal Artery Safety, Clin Res Cardiol (2011) 100:1095-1101.

Young, Robert R. et al, Reversible Block of Nerve Conduction by Ultrasound Ultrasonic Blocking of Nerve Fibers, Arch Neurol. 1961;4(1):83-89.

Zazgornik, Jan et al, Bilateral Nephrectomy: The Best, but Often Overlooked, Treatment for Refractory Hypertension in Hemodialysis Patients, AJH 1998; 11:1364-1370.

Ritz, Eberhard, New Approaches to Pathogenesis and Management of Hypertension, Clin J Am Soc Nephrol 4: 1886-1891, 2009.

Robbins, Ivan M. et al, Pulmonary Vein Stenosis After Catheter Ablation of Atrial Fibrillation, Circulation Journal of the American Heart Association, 1998;98:1769-1775.

Rocha-Singh, Krishna J., Catheter-Based Sympathetic Renal Denervation a Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Santos, Mario et al, Renal Sympathetic Denervation in Resistant Hypertension, World J Cardiol Apr. 26, 2013; 5(4): 94-101.

Savard, Sebastien et al, Eligibility for Renal Denervation in Patients With Resistant Hypertension When Enthusiasm Meets Reality in Real-Life Patients, J Am Coll Cardiol. 2012;60(23):2422-2424.

Schauerte, Patrick et al, Catheter Ablation of Cardiac Autonomic Nerves for Prevention of Vagal Atrial Fibrillation, Circulation Journal of the American Heart Association, 2000, 102:2774-2780.

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.

Schlaich, Markus P. et al, Renal Denervation as a Therapeutic Approach for Hypertension Novel Implications for an Old Concept, Hypertension Journal of the American Heart Association, 2009;54:1195-1201.

Schlaich, Markus P. et al, Renal Sympathetic-Nerve Ablation for Uncontrolled Hypertension, The New England Journal of Medicine, 2009; 361:932-934.

Schmieder, Roland E. et al, ESH Position Paper: Renal Denervation—An Iterventional Therapy of Resistant Hypertension, Journal of Hypertension, 2012, 30:837-841.

Schmieder, Roland E. et al, Updated EHS Position Paper on Interventional Therapy of Resistant Hypertension, EuroIntervention 2013; 9:R58-R66.

Sellers, Alfred M. et al, Adrenalectomy and Sympathectomy for Hypertension Ten Year Survival, Archives of Surgery, vol. 89, Nov. 1964, 880-886.

Sen, S.K., Some Observations on Decapsulation and Denervation of the Kidney, The British Journal of Urology, vol. 8, Issue 4, Dec. 1936, 319-328.

Shiraki, Iwao William, Correction of Renal Hypertension by Ligation of Stenotic Segmental Renal Artery, Urology, vol. IX, No. 3, Mar. 1977, 296-298.

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Smith, Harold P. et al, Radiofrequency Neurolysis in a Clinical Model Neuropathological Correlation, J Neurosurg 55:246-253, 1981.

Smithwick, R.H., An Evaluation of the Surgical Treatment of Hypertension, The Bulletin, Nov. 1949; 25(11):698-716.

Smithwick, Reginald H. et al, Splanchnicectomy for Essential Hypertension, The Journal of the American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.

Sowers, James R. et al, Diabetes, Hypertension, and Cardiovascular Disease: An Update, Hypertension Journal of the American Heart Association, 2001;37:1053-1059.

Stanley, James C., Surgical Treatment of Renovascular Hypertension, The American Journal of Surgery, vol. 174, Aug. 1997, 102-110.

Stella, Andrea et al, Effects of Reversible Renal Denervation on Haemodynamic and Excretory Functions of the Ipsilateral and Contralateral Kidney in the Cat, Journal of Hypertension 1986, 4: 181-188.

Stuart, Candace, Newest Frontier in Cardiac Care: Kidneys; Cardiovascular Business, Dec. 13, 2012.

Stuart, Mary, Masterminds of Ardian: An Interview With Inventors Mark Gelfand and Howard Levin, Windhover Information, Start-Up Jan. 1, 2011.

Sun, Yingxian et al, Risk of Coronary Stenosis with Venous Ablation for Epicardial Accessory Pathways, PACE, Apr. 2001, Part II, vol. 24, 605.

Swartz, John F. et al, Radiofrequency Endocardial Catheter Ablation of Accessory Atrioventricular Pathway Atrial Insertion Sites, Circulation Journal of the American Heart Association, 1993;87:487-499.

Teigen, Corey L. et al, Segmental Renal Artery Embolization for Treatment of Pediatric Renovascular Hypertension, Journal of Vascular and Interventional Radiology, 1992; 3:111-117.

Teixeira, Maria Do Carmo et al, 1992; Role of the Peripheral Renin Profile in Predicting Blood Pressure Control After Bilateral Nephrectomy in Renal-Transplanted Patients, Nephrol Dial Transplant (1998) 13: 2092-2097.

Teo, W S et al, Radiofrequency Catheter Ablation of Accessory Pathways: The Initial Experience in Singapore, Singapore Medical Journal, 1994; vol. 35:36-40.

Thiebot, J. et al, Bilateral Nephrectomy by Embolization of the Renal Arteries: A Report on Five Cases (author's transl), Sem Hop. Apr. 8-15, 1980;56(13-14):670-5.

Thomas, George et al, Renal Denervation to Treat Resistant Hypertension: Guarded Optimism, Cleveland Clinic Journal of Medicine, vol. 79, No. 7, Jul. 2012, 501-510.

Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.

Ting, Chih-Tai et al, Arterial Hemodynamics in Human Hypertension Effects of Angiotensin Converting Enzyme Inhibition, Hypertension Journal of the American Heart Association, 1993;22:839-846.

Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.

Valente, John F. et al, Laparoscopic Renal Denervation for Intractable ADPKD-Related Pain, Nephrol Dial Transplant (2001) 16:160.

Villarreal, Daniel et al, Effects of Renal Denervation on Postprandial Sodium Excretion in Experimental Heart Failure, American Journal of Physiology, May 1994;266(5 Pt 2):R1599-R1604.

Vonend, Oliver et al, Secondary Rise in Blood Pressure After Renal Denervation, The Lancet, vol. 380, Issue 9843, p. 778, Aug. 25, 2012.

(56) References Cited

OTHER PUBLICATIONS

Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.

Webb, R.L. et al, Functional Identification of the Central Projections of Afferent Renal Nerves, Clin. and Exper.—Theory and Practice, Ag(SUPPL.I), 47-57 (1987).

Weinstock, Marta et al, Renal Denervation Prevents Sodium Retention and Hypertension in Salt-Sensitive Rabbits with Genetic Baroreflex Impairment, Clinical Science (1996) 90, 287-293.

Wilcox, Josiah N., Scientific Basis Behind Renal Denervation for the Control of Hypertension, Medtronic, Inc., Dec. 2012, 38 pages.

Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.

Wolf-Maier, Katharina et al, Hypertension Treatment and Control in Five European Countries, Canada, and the United States, Hypertension. 2004;43:10-17.

Worthley, Stephen G. et al, Renal Denervation: How Do You Measure Success?, presentation 28 pages.

Wyss, J.M. et al, Sensory Denervation of the Kidney Attenuates Renovascular Hypertension in the Rat, Am J Physiol Heart Circ Physiol 250:H82-H86, 1986.

Yamada, Yutaka et al, Age-Related Changes in Muscle Sympathetic Nerve Activity in Essential Hypertension, Hypertension Journal of the American Heart Association, 1989;13:870-877.

International Search Report and Written Opinion for Application No. PCT/US2014/019421.

Abboud, Francois M., The Sympathetic System in Hypertension, State-of-the-Art Review, Hypertension Journal of the American Heart Association, Hypertension 4 (suppl II): II-208-II-225, 1982.

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.

Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.

Badoer, Emilio et al, Cardiac Afferents Play the Dominant Role in Renal Nerve Inhibition Elicited by Volume Expansion in the Rabbit, American Journal of Physiology, 1998, R383-R388.

Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.

Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.

Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.

Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.

Bello-Reuss, Elsa et al, Effects of Acute Unilateral Renal Denervation in the Rat, The Journal of Clinical Investigation, vol. 56, Jul. 1975, 208-217.

Benito, Fernando et al, Radiofrequency Catheter Ablation of Accessory Pathways in Infants, Heart, 1997, 78, 160-162.

Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.

Bertog, Stefan C. et al, Renal Denervation for Hypertension, JACC: Cardiovascular Interventions, vol. 5, No. 3, Mar. 2012, 249-258.

Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.

Blankestijn, Peter J. et al, Renal Denervation: Potential Impact on Hypertension in Kidney Disease?, Nephrol Dial Transplant (2011) 0: 1-3.

Blankestijn, Peter J. et al, Sympathetic Overactivity in Renal Failure Controlled by ACE Inhibition: Clinical Significance, Nephrol Dial Transplant, 2000, 15, 755-758.

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.

Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.

Brookes, Linda et al, Renal Denervation: Is Reality Meeting Expectations?, An Interview with Michel Azizi, MD, PhD, Medscape, Jan. 7, 2013.

Bunte, Matthew C. et al, Endovascular Treatment of Resistant and Uncontrolled Hypertension, JACC: Cardiovascular Interventions, vol. 6, No. 1, 2013, 1-9.

Calleary, Hickey D. et al, Pre-Transplant Bilateral Native Nephrectomy for Medically Refractory Hypertension, The Irish Medical Journal, Jul.-Aug. 2001;94(7):214-6.

Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.

Campese, V.M., Is Hypertension in Chronic Renal Failure Neurogenic in Nature?, Nephrol Dial Transplant, 1994, 9: 741-742.

Campese, Vito M. et al, Neurogenic Factors in Renal Hypertension, Current Hypertension Reports, 2002 4: 256-260.

Campese, Vito M. et al, Renal Afferent Denervation Prevents Hypertension in Rats With Chronic Renal Failure, Hypertension, 1995, 25, 878-882.

Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.

Campese, Vito M., Interventional Hypertension: A New Hope or a New Hype? The Need to Redefine Resistant Hypertension, J Hypertens. Nov. 2013;31(11):2118-21.

Canadian Agency for Drugs and Technologies in Health, Catheter-Based Renal Denervation for Treatment-Resistant Hypertension; Issues in Emerging Health Technologies, Issue 121, Mar. 2013.

Carlstedt, Thomas et al, Regrowth of Lesioned Dorsal Root Nerve Fibers into the Spinal Cord of Neonatal Rats, Neuroscience Letters Feb. 10, 1987;74(1)14-8.

Chabanier, H. et al, On the Decapsulation and Neurectomy of the Kidnesy in Permanent Hypertensive States, The Medical Press, Feb. 22, 1936, No. 16, 307-310.

Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.

Ciriello, John et al, Renal Afferents and Hypertension, Current Hypertension Reports 2002, 4:136-142.

(56) References Cited

OTHER PUBLICATIONS

Converse, Richard L. et al, Sympathetic Overactivity in Patients with Chronic Renal Failure, The New England Journal of Medicine, vol. 327, No. 27, 1992, 1912-1918.

Crile, George, The Clinical Results of Celiac Ganglionectomy in the Treatment of Essential Hypertension, Annals of Surgery, Jun. 1938; 107(6): 909-916.

Cruickshank, J.M., Beta-Blockers Continue to Surprise Us, European Heart Journal (2000) 21, 354-364.

Curtis, John J. et al, Surgical Therapy for Persistent Hypertension After Renal Transplantation, Transplantation, vol. 31, No. 2, 1981, 125-128.

Dailey, U.G., Surgical Treatment of Hypertension: A Review—Part II, Journal of the National Medical Association, May 1948, vol. 40, No. 3., 113-116.

Dailey, U.G., Surgical Treatment of Hypertension: A Review—Part III, Journal of the National Medical Association, Jul. 1948, vol. 40, No. 4, 160-162.

Dailey, U.G., The Surgical Treatment of Hypertension: A Review, Journal of the National Medical Association, Mar. 1948, vol. 40, No. 2, 76-79.

Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.

De Wardener, H.E., The Hypothalamus and Hypertension, Physiological Reviews, vol. 81, No. 4, Oct. 2001.

Dequattro V. et al, The Sympathetic Nervous System: The Muse of Primary Hypertension, Journal of Human Hypertension, 2002, 16 (Supp) 1), S64-S69.

Dibona, Gerald F. et al, Neural Control of Renal Function, Physiological Reviews, vol. 77, No. 1, Jan. 1997, 75-197.

Dibona, Gerald F. et al, Translational Medicine: The Antihypertensive Effect of Renal Denervation, Americal Journal of Physiology, 2010, 298, R245-R253.

Dibona, Gerald F., Neural Control of Renal Function: Cardiovascular Implications, Hypertension Journal of the American Heart Association, vol. 13, No. 6, Part 1, Jun. 1989, 539-548.

Dibona, Gerald F., Neural Control of the Kidney: Functionally Specific Renal Sympathetic Nerve Fibers, American Journal of Physiology, 2000, 279, R1517-R1524.

Hoshino et al., "Gelation of Poly(vinyl alcohol) in Dimethyl Sulfoxide/Water Solvent", Polymer Bulletin, 1996, 37, 237-244.

Mutoh et al. "A New Polyvinyl Alcohol Hydrogel Vascular Model (KEZLEX) for Microvascular Anastomosis Training", Surgical Neurology International, 2010,1:74.

Philipp et al., "Three Methods for In Situ Cross-Linking of Polyvinyl Alcohol Films for Application as Ion-Conducting Membranes in Potassium Hydroxide Electrolyte", NASA Technical Paper 1407, 1979.

* cited by examiner

THERMOCHROMIC POLYVINYL ALCOHOL BASED HYDROGEL ARTERY

BACKGROUND OF THE INVENTION

Ablation of blood vessels to interrupt the conduction of nerve signals in the body is known in the art. For example, renal denervation systems have been employed to ablate sympathetic renal nerves, which lie mainly on the adventitia of the renal artery with some nerves lying within the arterial wall itself, to treat hypertension. One such renal denervation system, the EnligHTN™ Multi-Electrode Renal Denervation System by St. Jude Medical Inc., is generally in the form of a catheter with a basket at the tip of the catheter, the basket including electrodes. The electrodes are inserted into a blood vessel, for example the renal artery, contact the inside wall of the blood vessel, and are activated with low-level radiofrequency ("RF") energy to ablate nerves in the blood vessel. The applied energy results in an increased temperature in the tissue and forms lesions in the wall of the blood vessel, interrupting conduction pathways that traverse the lesions.

It would be desirable to have an experimental model to provide verification of RF ablation systems in a simulated biological environment prior to any preclinical and clinical studies. The experimental simulation of RF ablation can predict achievable ablation lesions, patterns, and penetration depth, thus providing useful information for treatment planning and device performance.

BRIEF SUMMARY OF THE INVENTION

In one embodiment of the invention, a method of creating a thermochromic artificial tissue includes the step of physically cross-linking a polyvinyl alcohol solution in a mold shaped to mimic an animal tissue, such as a blood vessel, to create an artificial tissue. The artificial tissue is chemically cross-linked, and a coagulation solution is applied to the artificial tissue to both inhibit chemical cross-linking and promote physical cross-linking of the artificial tissue.

In another embodiment of the invention, a method of creating a thermochromic artificial blood vessel includes the step of physically cross-linking a polyvinyl alcohol solution in a mold shaped to mimic a blood vessel to create an artificial blood vessel, the polyvinyl alcohol solution including polyvinyl alcohol and water. The artificial blood vessel is then chemically cross-linked with a chemical cross-linking solution containing a chemical cross-linking reagent and water. A coagulation solution including water and a base is applied to the artificial blood vessel to both inhibit the chemical cross-linking and promote physical cross-linking of the artificial blood vessel. The polyvinyl alcohol solution may also include dimethyl sulfoxide, the chemical cross-linking reagent may be glutaraldehyde, and the base may be potassium hydroxide.

In a further embodiment of the invention, a method of testing an ablation catheter comprises the step of creating a thermochromic artificial blood vessel. To create the artificial blood vessel, a polyvinyl alcohol solution is physically cross-linked in a mold shaped to mimic a blood vessel, the polyvinyl alcohol solution including polyvinyl alcohol and water. The artificial blood vessel is then chemically cross-linked with a chemical cross-linking solution containing a chemical cross-linking reagent and water. A coagulation solution including water and a base is applied to the artificial blood vessel to both inhibit the chemical cross-linking and promote physical cross-linking of the artificial blood vessel. An ablation catheter is provided, the ablation catheter including one or more ablation elements configured to contact an inner wall of the artificial blood vessel. The ablation elements are inserted into a lumen of the artificial blood vessel and at least one of the ablation elements is contacted with the inner wall of the artificial blood vessel. Energy is emitted from at least one of the ablation elements. The extent of a change in at least one of a color or transparency of the artificial blood vessel is then determined.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Particular embodiments of the present disclosure are described with reference to the accompanying drawings. In the figures and in the description that follow, like reference numerals identify similar or identical elements. Volumes, percentages, temperatures and dimensions of materials and components disclosed herein are merely illustrative and variations thereof are within the scope of the invention.

Figure 1:
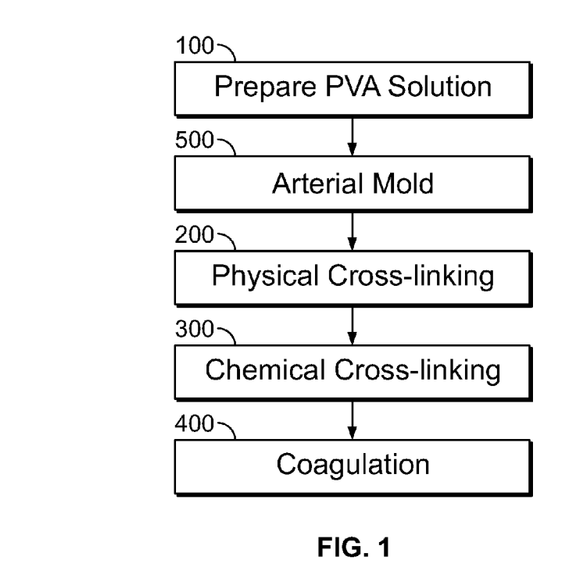
FIG. 1 illustrates a flow chart for preparing a PVA model artery according to one aspect of the invention.
Figure 2:
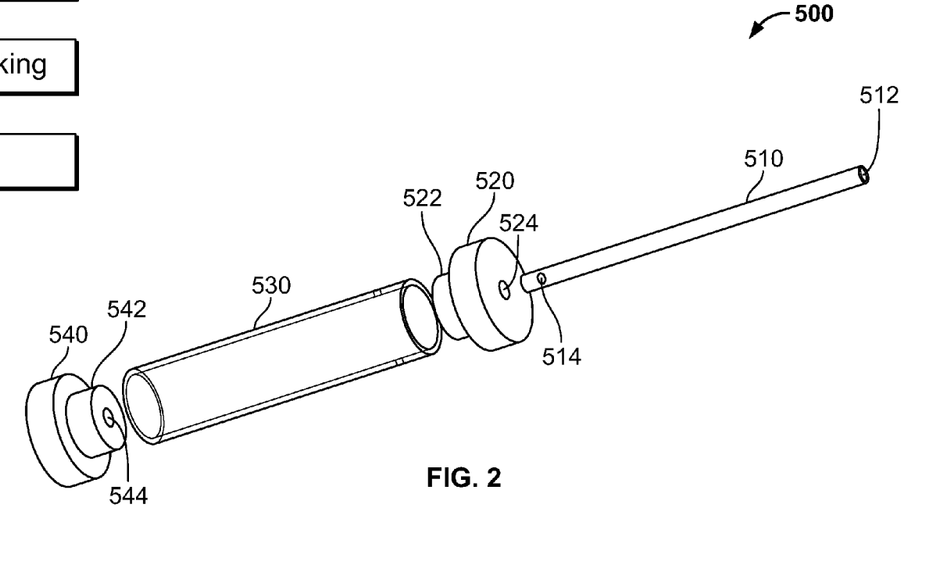
FIG. 2 illustrates an exploded unassembled perspective view of a model artery mold according to an aspect of the invention.
Figure 3A:
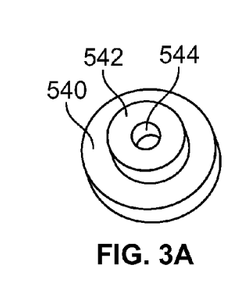
FIGS. 3A-D illustrate the components of the model artery mold of FIG. 2.
Figure 3B:
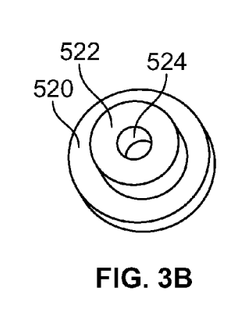
Figure 3C:
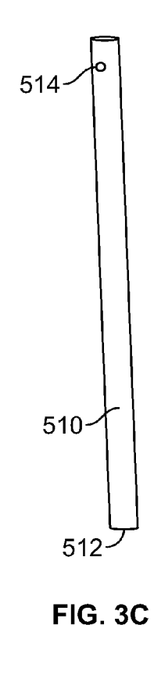
Figure 3D:
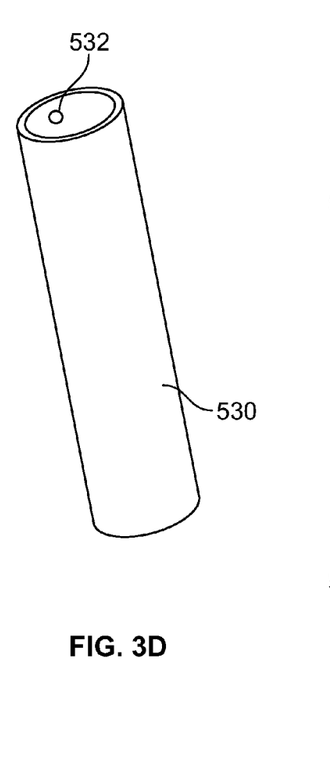

According to one aspect of the disclosure, a polyvinyl alcohol ("PVA") polymer solution is prepared and processed in conjunction with a mold to form a thermochromic PVA polymer-based artificial artery that can serve as an experimental model of a human artery. The model artery can be molded to emulate various artery sizes and shapes to replicate different human tissues and organs for bench testing of ablation devices. To create the model artery, generally referring to FIG. 1, the user first prepares a PVA solution 100. Once prepared, the user performs physical cross-linking 200 using an arterial mold 500, resulting in a PVA model artery 700 such as that shown in FIG. 6. Once created, the PVA model artery 700 undergoes chemical cross-linking 300 and coagulation 400 of the PVA in the model artery. Once the model artery 700 is treated, the user can perform an ablation step on the model artery 700 with an ablation device 20 such as a RF renal denervation catheter, such as that shown in FIG. 7. As the ablation device 20 heats the model artery, the color and/or transparency of the model artery 700 changes to indicate the degree of heating.

The following descriptions, including the cross-linking and coagulation steps and related solution preparations, are merely exemplary of embodiments of the invention and may be varied, such variations still being within the scope of the invention.

PVA Solution Preparation

According to one aspect of the disclosure, a 500 mL 10% w/v PVA solution is prepared in the PVA preparation step 100. In the PVA preparation step 100, 400 mL of water is combined with 100 mL of dimethyl sulfoxide ("DMSO") to form a DMSO-water mixture. The DMSO, for example, may be that sold as Sigma-Aldrich D5879. Preferably, the water is purified by reverse osmosis or deionization. Approximately 50 g of PVA is weighed out and set aside. Preferably, the PVA has a molecular weight of approximately 146,000 to 186,000 and is very pure, for example 99% or more hydrolyzed. Less pure PVA may be used, for example PVA that is 95% or more hydrolyzed, or PVA that is 90% or more hydrolyzed. Consequences of using less pure PVA are discussed below. The PVA, for example, may be that sold as Sigma-Aldrich 363065. Approximately 250 mL of the DMSO-water mixture is added to a jar and then heated, for example, by placing the jar in a heated water bath on a hot plate between about 75°-85° C., or approximately 80° C. This temperature may vary, but is generally effective to cause dissolution of the PVA. The PVA is added to the heated jar. The PVA may be added slowly and manually or automatically stirred, for example with a magnetic stirring bar. The remaining DMSO-water mixture is added to the jar until the total volume of the solution is approximately 500 mL. Stirring and heating is continued until the PVA polymers are dissolved.

The DMSO functions to modify the PVA gelation process to make the resulting PVA model artery 700 transparent. The addition of DMSO-water solvents to PVA is known to affect the turbidity of the resulting PVA gel by, for example, altering the crystallinity of the PVA. Varying the DMSO composition can lead to the formation of a transparent or opaque PVA gel. The effect of DMSO-water solvents on PVA gelation is described more fully in Hoshino et al., Gelation of Poly(Vinyl Alcohol) in Dimethyl Sulfoxide/Water Solvent, Polymer Bulletin 37, 237-244 (1996), the entire contents of which are hereby incorporated by reference herein.

If air bubbles are present, the solution may optionally be de-gassed, for example, by using an ultrasonic bath at around 60-70° C. for approximately 30 minutes or until air bubbles are no longer present. Gelatin may also be added to the PVA solution to provide structural integrity at a low concentration, preferably between about 2% and 5%. Other additives, such as polyacrylic acid, may also be added to the PVA solution instead of or in addition to gelatin to provide varying levels of structural integrity to the PVA model artery 700. U.S. Pat. No. 5,972,375, the entire contents of which are hereby incorporated by reference herein, further discusses alternative agents, in addition or alternative to gelatin, that may be added to the PVA solution.

Although a 500 mL 10% w/v PVA solution is described, more or less PVA solution may be prepared depending on the particular application. While a 10% w/v PVA solution is preferred, the PVA solution may range from approximately 3% to approximately 40%. Because lower concentrations may require additional freezing-thawing cycles, it would be preferred to have a PVA solution with a concentration between about 10% w/v and 40% w/v. Similarly, although the DMSO-water ratio is described as 20%:80%, the DMSO-water solution may range from about 10%:90% to about 30%:70%. Other polar aprotic solvents may be substituted for DMSO, including, for example, dimethylformamide (DMF). The PVA solution may be stored at room temperature until it is to be used. If the solution becomes solid, it may be re-warmed to re-dissolve the PVA solution. Although the PVA solution is described as including DMSO, the PVA model artery 700 may be created without the use of DMSO. Table 1 illustrates exemplary volumes and masses of PVA, water and DMSO in 10% PVA solutions for various total volumes. This table should be understood to be merely representative of possible PVA solutions, and not limiting in any way.

TABLE 1

| Total Volume (mL) | PVA (g) | Water (mL) | DMSO (mL) |
|---|---|---|---|
| 050 | 5 (±0.05) | 40 | 10 |
| 100 | 10 (±0.1) | 80 | 20 |
| 150 | 15 (±0.15) | 120 | 30 |
| 200 | 20 (±0.2) | 160 | 40 |
| 500 | 50 (±0.5) | 400 | 100 |
| 1000 | 100 (±1) | 800 | 200 |

Arterial Mold

The arterial mold 500, as illustrated in FIGS. 2-5, generally includes a hollow mandrel 510, a mold top 520, a tube 530, and a mold bottom 540. The tube 530 is generally cylindrical, open at both ends, and provides an outer shape of the model artery. Preferably, the tube 530 is transparent so that a user can view the PVA solution in the mold 500 as well as components within the mold. Various materials, such as polycarbonate or acrylic, may be used to form the tube 530. Preferably, the material for the tube 530 has a smooth inner surface such that the PVA model artery 700, when formed, correspondingly has a smooth outer surface. The tube 530 includes a vent hole 532 near the top end of the tube. When the mold 500 is assembled and PVA solution is introduced into the mold, the vent hole 532 allows for pressure equalization in the mold.

Mold top 520 includes a generally cylindrical base larger than the diameter of the tube 530. Mold top 520 also includes a smaller cylindrical portion 522 configured to fit within tube 530. Mold top 520 further includes a recess 524. Recess 524 is hollow and extends through the entirety of mold top 520. The mandrel 510 can pass through the mold top 520 via recess 524 and into tube 530 when the mold top is inserted in the tube. Mold bottom 540 is configured similarly to mold top 520, with a relatively large base, relatively small cylindrical portion 542, and a recess 544. Recess 544 extends only partially through mold bottom 540, such that mandrel 510 can pass into the recess, but not through the entirety of the mold bottom. The mold top 520 and mold bottom 540 may be formed from various materials such as thermoplastics. For example, polyoxymethylene, sold by DuPont under the name Delrin®, may be suitable for use in forming the mold top 520 and mold bottom 540.

Hollow mandrel 510 is cylindrical with a solution outlet 514 in the form of an aperture near the closed bottom and a solution inlet 512 at the top. Hollow mandrel 510 may be formed essentially of any rigid material. For example, stainless steel may be suitable to form the hollow mandrel 510. The solution inlet 512 is formed by the hollow interior of the mandrel 510. The mandrel 510 is sized in diameter to snugly pass through the recess 524 in the mold top 520 and into the recess 544 in the mold bottom 540. When positioned through the mold top 520 and in the mold bottom 540, the top of the mandrel 510 extends above the mold top such that the solution inlet 512 of the mandrel is easily accessible.

Although a particular embodiment of the mold 500 is described above, features of components of the mold may be added, removed, or modified. For example, the recess 544 in mold bottom 540 may be removed in one embodiment. In other embodiments, the mandrel 510 may be solid. A person of skill in the art would recognize modifications of the described embodiment that would still allow for molding of a model artery 700 or other tissue.

Although the mold 500 described above takes a form to mimic a human artery, other shapes, including arteries and tissues more generally, are contemplated. For example, a bifurcated mold may be used to create a bifurcated PVA model artery. The bifurcated PVA model artery may be especially useful in testing RF ablation devices, as the renal artery bifurcates to connect to the left and right kidneys. Similarly, other the shape of other tissues may be mimicked using any range of molds 500. Other non-tissue shapes may also be useful. For example, a dog-boned shape mold may be used to create a dog-bone shaped PVA model. A single batch of solution may be used to create a number of PVA model arteries and a dog-bone shaped PVA model. The dog-bone shaped PVA model may be used to test mechanical properties of the PVA model, such as stress-strain curves, which would also represent the mechanical properties of the remaining PVA model arteries created from the same batch of solution. For example, if a batch of ten model arteries and one dog-bone shaped PVA model was created from a single batch of solution, the dog-bone PVA model may be used for standard mechanical testing to determine, for example, the Young's modulus of the dog-bone PVA model. The Young's modulus value of the dog-bone PVA model would be representative of the Young's modulus for the remaining ten model arteries created from the same batch.

Figure 4:
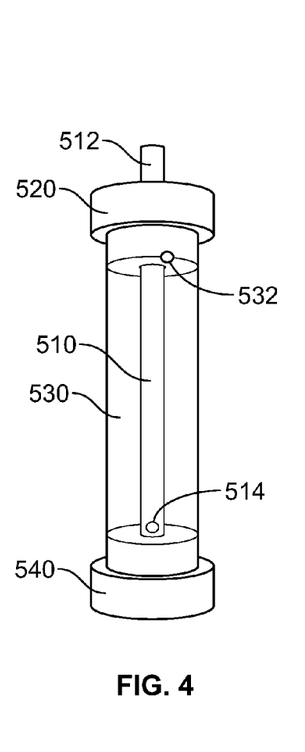
FIG. 4 illustrates the model artery mold of FIG. 2 in an assembled condition.
Figure 5:
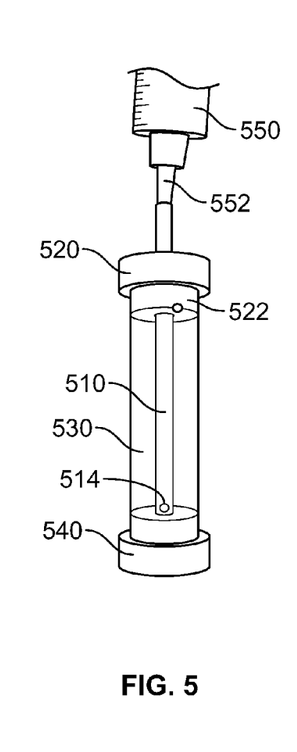
FIG. 5 illustrates filling the assembled model artery mold of FIG. 4 with PVA solution.

Prior to the physical cross-linking step 200, the mold 500 is assembled, as illustrated in FIG. 4, with the mold top 520 and mold bottom 540 coupled to the tube 530, and mandrel 510 inserted through the mold top, through the tube, and into the mold bottom. A syringe 550, as shown in FIG. 5, is filled with dissolved PVA solution obtained from the PVA solution preparation step 200. If the PVA solution has become solid prior to filling the syringe 550, the PVA solution may be re-dissolved by heating the solution back to approximately 80° C. A syringe tip 552 is inserted into the solution inlet 512 of the mandrel 510 and the PVA solution is injected into the mold 500. The solution travels down the hollow mandrel 510, exits the mandrel at the solution outlet 514, and fills the space between the mandrel and the tube 500. As filling occurs, air in the tube 530 is forced out through the vent hole 532. Although the filling method is described with respect to the embodiment of the mold 500 described above, other filling methods may be used with other embodiments of the mold. For example, if a solid mandrel is used, the filling may take place surrounding the mandrel rather than through the mandrel.

Once the mold 500 is filled with PVA solution, air bubbles, if present, may be removed by immersing the filled mold in an ultrasonic bath for about 20 minutes or longer if air bubbles do not disappear after 20 minutes. If placed in the ultrasonic bath, care should be taken to ensure the mold 500 is standing vertically to ensure the PVA solution does not leak out of the mold through solution inlet 512. The filled mold 500 is then immersed in a water bath at approximately 37-40° C. for about 20 minutes and then brought to room temperature for at least 20 minutes. The water bath and room temperature steps may be useful for bringing a plurality of samples to the same temperature prior to the physical cross-linking step, described in further detail below. The times and temperatures provided here, as elsewhere provided, are merely illustrative, may be varied, and are not intended to limit the scope of the invention.

Physical Cross-Linking

In the physical cross-linking step 200, the PVA solution is physically cross-linked to form a crystalline or semi-crystalline structure, in the shape of a human artery, via freezing-thawing processes. In part, the physical cross-linking step 200 provides elasticity to the PVA solution similar to human arteries and further provides a base level of structural integrity. The arterial mold 500 is assembled prior to the physical cross-linking of the PVA solution.

After the filled mold 500 is at room temperature, the mold is repeatedly frozen and thawed. For example, the mold may be frozen by placing the mold in a freezer between about −15 and −25° C., or approximately at −20° C., for about 15-17 hours. The mold may then be thawed at room temperature between about 15-25° C., or approximately at 20° C. for about 7.5-8.5 hours. The freezing step and thawing steps are preferably repeated once, but may be repeated more than once or not at all. For example, additional freezing cycles may result in better physical formation of the PVA gel into the structure of the mold and an increase in mechanical properties of the gel, such as Young's modulus. Further, if the PVA solution is less pure (e.g. 95% hydrolyzed instead of 99% hydrolyzed), further repetition of the freezing and thawing steps may be desired to help ensure complete physical cross-linking. For example, 90% hydrolyzed PVA solution may require more than two cycles of freezing and thawing for physical cross-linking to occur. It should be understood that various freezing and thawing time and temperatures may be used depending on the particular solutions used. For example, the PVA solution may begin to gain physical integrity with as little as 4 hours of freezing. The specific freezing and thawing times and conditions may be determined by one of skill in the art.

Figure 6:
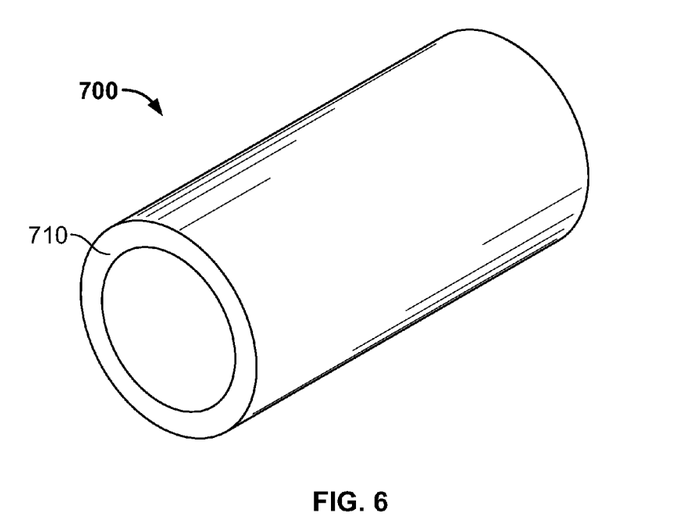
FIG. 6 illustrates a perspective plan view of a PVA model artery.

After completing the freezing and thawing steps, the physical cross-linking step 200 is complete, and the PVA model artery 700, as illustrated in FIG. 6, is removed from the mold 500. Applying a small amount of water to the PVA model artery 700 in the mold 500 may make it easier to remove the PVA model artery 700 form the mold. At this point, the PVA model artery 700 is generally transparent and susceptible to heat degradation.

Different sizes and shapes of molds 500 may be used depending on the particular vessel or tissue to be modeled. For example, 1 mm and 5 mm thick molds 500 may be useful in modeling the renal vasculature, including the renal artery. As used herein, the thickness refers to the dimension between the outer surface of the mandrel 510 and the inner surface of tube 530. This dimension is equivalent to the thickness of a wall 710 of the PVA model artery 700 that will result from the physical cross-linking step 200 in mold 500.

Chemical Cross-Linking

After the PVA model artery is formed through the physical cross-linking step 200, a chemical cross-linking step 300 is performed. Chemically cross-linking the PVA model artery, in part, provides additional structural integrity as well as heat resistance. Without the chemical cross-linking step 300, the heat created during an experimental ablation procedure could melt the PVA model artery 700. A mild chemical cross-linking is enough for PVA gels to maintain structural integrity against heat while still maintaining mechanical elasticity.

Prior to performing the chemical cross-linking step 300, a chemical cross-linking solution must be prepared. The chemical cross-linking reagent, for example, may be a glutaraldehyde ("GTA") solution in an acidic environment. The chemical cross-linking solution may also include sodium sulfate ($Na_2SO_4$). The GTA solution, for example, may be a 50% GTA solution sold as Fisher Scientific BP2547. The $Na_2SO_4$, for example, may be that sold as Fisher Scientific 5429. In one example, a 500 mL 2% GTA with $Na_2SO_4$ solution may be prepared for the chemical cross-linking step 300. Because a mild chemical cross-linking is sufficient, a relatively low concentration of GTA may be used. In this example, 480 mL of water, preferably water purified by reverse osmosis or deionization, is added to a container. 20 mL of 50% GTA is added to the container with 480 mL of water. 5 mL of concentrated sulfuric acid ($H_2SO_4$) is then added to the water-GTA solution. The $H_2SO_4$, for example, may be that sold as Fischer Scientific A484-212. Approximately 50 g of $Na_2SO_4$ anhydrous is then added to the water-GTA-$H_2SO_4$ solution and the mixture is stirred until the $Na_2SO_4$ anhydrous is dissolved. The acidic environment provided by the sulfuric acid and sodium sulfate helps stimulate chemical cross-linking of the PVA model artery 700. Concentrated acids are preferred to reduce the total volume of acid that needs to be handled. Other acids besides sulfuric acid may be used to reach the goal of a chemical cross-linking solution with an acidic pH.

Although a 500 mL 2% GTA with $Na_2SO_4$ solution is described, more or less volume of solution may be prepared depending on the particular application. Similarly, other percentage GTA with $Na_2SO_4$ solutions may be prepared. For example, a 5% GTA with $Na_2SO_4$ solution may be preferable for particular applications, and up to 25% GTA with $Na_2SO_4$ solution may be used, although the higher percentage GTA solutions may begin to result in a decreased elasticity. Other dialdehydes may be used instead of GTA, although the toxicity of other dialdehydes may be a relevant factor in determining whether substitution is appropriate. Further, although 1% $H_2SO_4$ v/v and 10% $Na_2SO_4$ w/v is described, the exact amount of each in the chemical cross-linking solution may be modified. Similarly, other acids, especially strong acids, may be used in place of $H_2SO_4$, to create the desired acidic environment for cross-linking. If the chemical cross-linking solution is to be stored, preferably it is stored at room temperature protected from light. Table 2 illustrates exemplary volumes and masses of components of a 2% GTA with $Na_2SO_4$ solution and a 5% GTA with $Na_2SO_4$ solution. This table should be understood to be merely representative of possible cross-linking solutions, and not limiting in any way.

TABLE 2

| Total volume (mL) | [GTA] (%) | Water (mL) | 50% GTA (mL) | $H_2SO_4$ (mL) | $Na_2SO_4$ (g) |
|---|---|---|---|---|---|
| 500 | 2 | 480 | 20 | 5 | 50 ± 0.5 |
| 1000 | 2 | 960 | 40 | 10 | 100 ± 1 |
| 2000 | 2 | 1920 | 80 | 20 | 200 ± 2 |
| 500 | 5 | 450 | 50 | 5 | 50 ± 0.5 |
| 1000 | 5 | 900 | 100 | 10 | 100 ± 1 |
| 2000 | 5 | 1800 | 200 | 20 | 200 ± 2 |

Once the cross-linking solution is prepared, and the PVA solution has undergone the physical cross-linking step 200, the chemical cross-linking step 300 may begin. In the chemical cross-linking step 300, the PVA model artery 700 is placed in a container and immersed in the cross-linking solution. The optimum cross-linking solution used and time of immersion may depend on the thickness of the PVA model artery wall 710. For example, if a mold 500 with 1 mm thickness was used to create the PVA model artery 700, the chemical cross-linking preferably entails immersing the PVA model artery in a 2% GTA with $Na_2SO_4$ solution for about between 9-11 minutes, preferably 10 minutes. If a mold 500 with 5 mm thickness was used to create the PVA model artery 700, the chemical cross-linking preferably entails immersing the PVA model artery in a 5% GTA with $Na_2SO_4$ solution for about between 18-22 minutes, preferably 20 minutes. The chemical cross-linking may be performed at room temperature, for example between about 15-25° C., or approximately 20° C. As the chemical cross-linking is taking place, it may be desirable to gently shake the container housing the PVA model artery 700 and cross-linking solution. It should be understood that the specific concentration of cross-linking solution and time of immersion may vary and the examples given above are merely illustrative and not limiting. After chemical cross-linking is complete, the PVA model artery 700 will likely have changed from transparent to slightly opaque, but still translucent and is more heat-resistant compared to before the chemical cross-linking step 300.

Coagulation

After the chemical cross-linking step 300 is complete, a third cross-linking step, the coagulation step 400, may be performed. The coagulation step 400 stops the PVA model artery from forming further chemical cross-links while also providing additional physical cross-linking of PVA macromolecular chains due to the compositions of the coagulation solution described below.

Prior to performing the coagulation step 400, a coagulation solution must be prepared. The coagulation solution, for example, may be a potassium hydroxide (KOH) and $Na_2SO_4$ solution. The KOH may be, for example, that sold as Fischer Scientific P250. KOH is a base that functions to deactivate the PVA from forming further chemical cross-links. $Na_2SO_4$ in the solution provides for additional physical cross-linking or interaction between PVA chains as a result of sulfate ions removing water from the PVA gel. Essentially $Na_2SO_4$ has a salting out effect, pushing water out of the PVA gel. In one example, 1000 mL of coagulation solution with about 7.5% w/v KOH is prepared for the coagulation step 400. In this example, approximately 75 g of KOH is added to a container with 900 mL of water, preferably water purified by reverse osmosis or deionization. About 142 g of $Na_2SO_4$ anhydrous, is added to the KOH-water solution. Water is added to the solution until the final volume is approximately 1000 mL. The contents are mixed until the $Na_2SO_4$ is dissolved.

Although a 1000 mL solution of 7.5% w/v KOH with 1M of $Na_2SO_4$ is described, more or less coagulation solution may be prepared depending on the particular application. Also, while a 7.5% w/v KOH coagulation solution is described, the coagulation solution may include higher or lower percent of KOH, for example 1% KOH may be desirable. Similarly, more or less $Na_2SO_4$ may be used than that which is described, as one of skill in the art would determine. Alternatives to $NA_2SO_4$ may also be used, as known by one of skill in the art. For example, sodium fluoride or $NA_2HPO_4$ may be used instead of $NA_2SO_4$. Similarly, any strong base may be effective as an alternative to KOH. Table 3 illustrates exemplary volumes and masses of KOH, $Na_2SO_4$, and water in a 7.5% w/v KOH solution with $Na_2SO_4$. This table should be understood to be merely representative of possible coagulation solutions, and not limiting in any way.

TABLE 3

| Total volume (mL) | Water (mL) | KOH (g) | $Na_2SO_4$ (g) |
|---|---|---|---|
| 500 | 500 | 37.5 ± 0.38 | 71.02 ± 0.71 |
| 1000 | 1000 | 75 ± 0.75 | 142.04 ± 1.42 |
| 2000 | 2000 | 150 ± 1.5 | 284.08 ± 2.84 |

Once the coagulation solution is prepared, and the PVA solution has undergone the physical cross-linking step 200 and the chemical cross-linking step 300, the coagulation step 400 may begin. In the coagulation step 400, the PVA model artery 700 is placed in a container and immersed in the coagulation solution. The PVA model artery 700 and coagulation solution are incubated for a period of time depending on the size of the PVA model artery. For example, if a mold 500 with 1 mm thickness was used to create the PVA model artery 700, the coagulation step 400 preferably entails immersing the PVA model artery in the coagulation solution for about 13-17 minutes, preferably 15 minutes. If a mold 500 with 5 mm thickness was used to create the PVA model artery 700, the coagulation step 400 preferably entails immersing the PVA model artery in the coagulation solution for about 54-66 minutes, preferably 60 minutes. In all cases, it is preferable that every 6-9 minutes, preferably every 7.5 minutes, the PVA model artery 700 is placed into fresh coagulation solution. The coagulation step may be performed at between about 15-25° C., or approximately 20° C. As the coagulation step 400 is taking place, it may be desirable to gently shake the container housing the PVA model artery 700 and coagulation solution. It should be understood that the specific concentration of components in the coagulation solution, temperatures, and times of immersion may vary and the examples given above are merely illustrative and not limiting. After the coagulation step 400 is complete, the PVA model artery will likely have changed from slightly opaque to white, while still being somewhat translucent.

Finally, prior to use, the PVA model artery should be washed, preferably in saline buffer. For example, if a mold 500 with 1 mm thickness was used to create the PVA model artery 700, the PVA model artery should be immersed in saline buffer for about 18-22 minutes, preferably 20 minutes, and the process repeated up to three times. If a mold 500 with 5 mm thickness was used to create the PVA model artery 700, the PVA model artery should be immersed in saline buffer for about 18-22 minutes, preferably 20 minutes, and the process repeated up to six times. The washing step may be performed, for example, at between about 15-25° C., or approximately 20° C. The PVA model arteries may be stored in saline buffer prior to use, preferably in a refrigerator, for example at about 4° C. The washing step may be omitted or the parameters of washing altered while still remaining within the scope of the invention.

RF Ablation Testing

Figure 7:
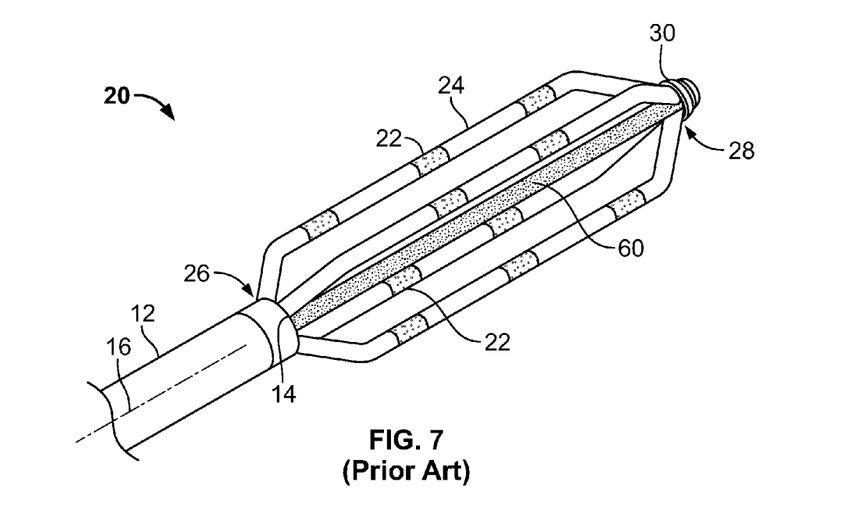
FIG. 7 illustrates a perspective view of an ablation device.

Once the PVA model artery 700 is formed and has been processed through all the cross-linking and washing steps, it may be used in conjunction with an ablation device 20, such as an RF ablation device, as illustrated in FIG. 7. In this particular ablation device 20, the ablation device includes an elongated catheter body 12 extending longitudinally between a proximal end (not shown) and a distal end 14 along a longitudinal axis 16. A basket assembly includes a plurality of ablation elements 22, such as RF electrodes, connected to the catheter body 12. The basket assembly includes a plurality of spines 24, which may be oriented generally longitudinally. Each spine 24 has a proximal end 26 connected to the catheter body 12 and a distal end 28. The distal ends 28 of the spines 24 are connected to a spine distal junction 30. A longitudinal rod 60 in the center of the basket assembly is connected to the spine distal junction 30, and can be used to pull the spine distal junction 30 toward the distal end 14 of the catheter body 12 to move the basket assembly from a collapsed condition to an expanded condition. This particular ablation device 20 is described in more detail in U.S. Patent Publication No. 2011/0118726, the entire contents of which are hereby incorporated by reference herein. Other devices besides RF ablation devices such as the one illustrated in FIG. 7 may be used in conjunction with the PVA model artery 700 or other PVA model tissues, especially devices that act to transmit heat or cause a material to heat or cool.

The ablation device is inserted into an artery or other blood vessel in the collapsed condition and steered to a location where ablation is desired. Once at the appropriate location, the user can manipulate longitudinal rod 60 to move the basket assembly to the expanded condition in which the electrodes 22 contact the inner wall of the artery. Energy is applied through a generator or other device (not shown) connected to the proximal end of the catheter 12 to provide the ablation energy.

Figure 8A:
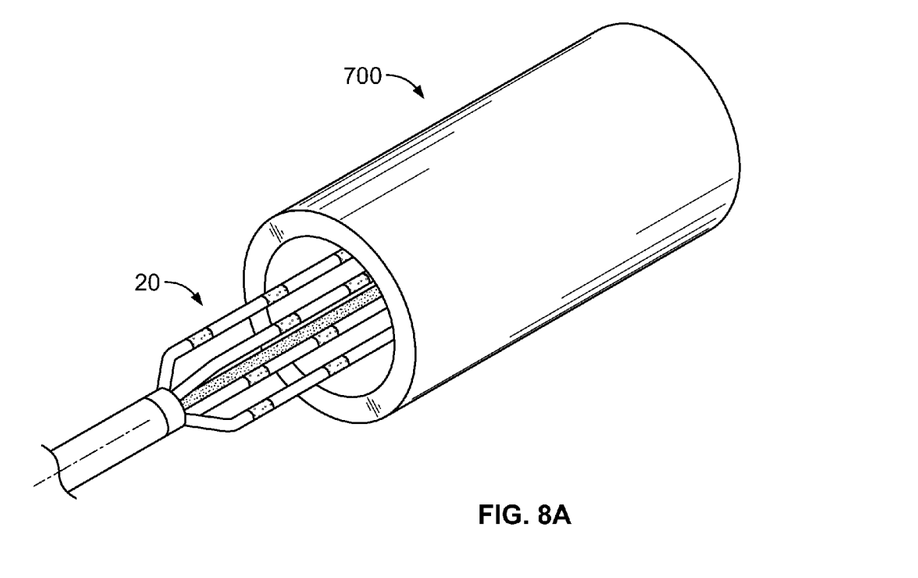
FIG. 8A illustrates the ablation device of FIG. 7 inserted into the PVA model artery of FIG. 6.

To experiment with the ablation device 20, a user inserts the ablation device into the PVA model artery 700 prepared as described above. The ablation device 20 entering the PVA model artery 700 prior to ablation energy being emitted is illustrated in FIG. 8A. While inserting the ablation device 20, the user is able to visualize the ablation device through the PVA model artery 700. This visualization is possible because, although the PVA model artery 700 is generally white and/or partially opaque, it is also transparent enough to visualize the device. The user manipulates the ablation device into the desired location and applies energy through the electrodes 22 in contact with the interior of the PVA model artery 700. The PVA model artery 700 possesses electrical ionic conductive properties similar to live tissue by virtue of the PVA. As energy is transmitted from the ablation elements 22 to the PVA, resistance causes a local increase in temperature of the PVA model artery 700 near the ablation elements. Because of the chemical cross-linking step 300 during preparation of the PVA model artery 700, the PVA model artery is able to withstand the heat without dissolving. Also, because of the coagulation step 400 during preparation of the PVA model artery 700, the color of the PVA model artery changes at locations where the temperature of the PVA increases, depending on the intensity of the heat.

Figure 8B:
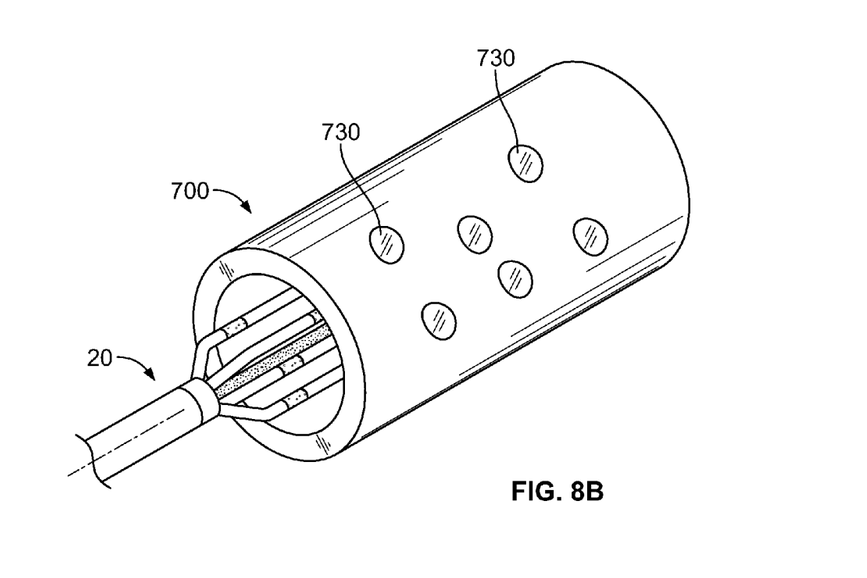
FIG. 8B illustrates the PVA model artery of FIG. 6 after performing ablation.

As temperatures of the PVA model artery 700 increase, as illustrated in FIG. 8B, model lesions 730 appear at the points where temperatures increase the most, the model lesions being more translucent than the remainder of the PVA model artery. Although the relationship between color change and temperature depends in part on the specific procedures used to create the PVA model artery 700, preferably there is little or no change at about 50° C., a slight change from white to translucent at about 65° C., and a change from translucent to transparent at about 70° C. The composition of the PVA solution may be altered by a person of skill in the art to create model arteries or tissues that change color and/or transparency at different temperature ranges than disclosed above, depending on the particular purpose of the testing.

The model lesions 730 created in the PVA artery model 700 by the ablation device 20 mimic the lesions that would be created by the same ablation device using the same procedure on a human artery after which the PVA artery model is modeled. This provides for analysis of effectiveness and safety of a variety of procedures using the ablation device 20 that are repeatable, provide for simple and standardized analysis, and use customizable materials. Optical measurements may be used, for example, to determine the boundaries of the model lesions 730, as well as the relative transparency of the model lesions, where increased transparency correlates to higher temperatures in the PVA model artery 700. The depth of the model lesions 730 may also be relevant in determining the effectiveness of the RF ablation device 20.

To more closely mimic an RF ablation procedure in a human, the above testing procedure may be performed while the PVA model artery 700 is connected to a pump. The pump, for example, may operate as a constant flow pump or a pulsatile pump, and may pump a saline solution, animal blood, or other fluid through the PVA model artery 700 during RF ablation. The goal is to mimic the flow of blood through an artery that would be occurring during RF ablation of a living patient. The effects of such flow may be significant, as a flowing fluid will alter the heat transfer properties of the system. A pulsatile pump may be preferred over a constant flow pump to mimic the flow of blood through an artery in a patient caused by a beating heart.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. Similarly, aspects described with reference to certain described embodiments may be combined with aspects described in other embodiments without departing the scope of the invention.

The invention claimed is:

1. A method of creating a thermochromic artificial blood vessel, the method comprising:
   physically cross-linking a polyvinyl alcohol solution at a temperature below 0° C. in an arterial mold so as to form an artificial blood vessel, the polyvinyl alcohol solution including polyvinyl alcohol and water;
   chemically cross-linking the physically cross-linked blood vessel with a chemical cross-linking solution, the chemical cross-linking solution including a chemical cross-linking reagent and water; and
   applying a coagulation solution to the chemically cross-linked blood vessel to both inhibit the chemical cross-linking and promote physical cross-linking of the artificial blood vessel, thereby imparting to the artificial blood vessel the ability to change color and/or transparency at locations thereof where temperature increases, the coagulation solution including water, a base, and a cross-linking promoter.

2. The method of claim 1, wherein the polyvinyl alcohol solution further comprises dimethyl sulfoxide, the chemical cross-linking reagent is glutaraldehyde, the base is potassium hydroxide, and the cross-linking promoter is sodium sulfate.

3. A method of creating a thermochromic artificial tissue, the method comprising steps of:
   physically cross-linking a polyvinyl alcohol solution by freeze-thawing in a mold shaped to mimic an animal tissue so as to create the artificial tissue;
   chemically cross-linking the physically cross-linked tissue with a chemical cross-linking solution comprising a chemical cross-linking reagent; and
   applying a coagulation solution to the chemically cross-linked tissue to both inhibit the chemical cross-linking and promote physical cross-linking of the artificial tissue, thereby imparting to the artificial tissue the ability to change color and/or transparency at locations thereof where temperature increases.

4. The method of claim 3, wherein the artificial tissue comprises an artificial blood vessel.

5. The method of claim 4, wherein the polyvinyl alcohol solution includes polyvinyl alcohol and water.

6. The method of claim 5, wherein the polyvinyl alcohol has a molecular weight of between about 146,000 to 186,000 Daltons.

7. The method of claim 6, wherein the polyvinyl alcohol is at least about 99% hydrolyzed.

8. The method of claim 5, wherein the polyvinyl alcohol solution further comprises dimethyl sulfoxide.

9. The method of claim 3, wherein said freeze-thawing is repeated at least once.

10. The method of claim 4, wherein the chemical cross-linking solution comprises water.

11. The method of claim 10, wherein the chemical cross-linking reagent is glutaraldehyde.

12. The method of claim 11, wherein the chemical cross-linking solution further includes a pH modifying agent.

13. The method of claim 12, wherein the pH modifying agent is sulfuric acid.

14. The method of claim 4, wherein the coagulation solution includes water, a base, and a cross-linking promoter.

15. The method of claim 14, wherein the base is potassium hydroxide.

16. The method of claim 15, wherein the cross-linking promoter is sodium sulfate.

* * * * *